United States Patent [19]

Dory

[11] 4,209,022
[45] Jun. 24, 1980

[54] ECHOGRAPHY APPARATUS FOR MEDICAL DIAGNOSIS, USING A MULTIPLE-ELEMENT PROBE

[75] Inventor: Jacques Dory, Meaux, France

[73] Assignee: CGR Ultrasonic, France

[21] Appl. No.: 796,637

[22] Filed: May 13, 1977

[30] Foreign Application Priority Data

Jun. 3, 1976 [FR] France ................... 76 16744

[51] Int. Cl.² ............................................. A61B 10/00
[52] U.S. Cl. .................................... 128/660; 73/626; 73/614
[58] Field of Search .......... 128/2 V, 2.05 Z, 660–663; 73/618–621, 624–626, 614

[56] References Cited

U.S. PATENT DOCUMENTS

| 3,577,772 | 5/1971 | Perilhou et al. | 128/2 V X |
|---|---|---|---|
| 3,777,740 | 12/1973 | Hokanson | 128/2 V |
| 3,792,423 | 2/1974 | Becker et al. | 73/620 |
| 3,856,985 | 12/1974 | Yokoi et al. | 128/2 V X |
| 3,872,858 | 3/1975 | Hudson et al. | 128/2 V |
| 3,881,466 | 5/1975 | Wilcox | 128/2.05 Z X |
| 3,924,452 | 12/1975 | Meyer et al. | 73/621 |
| 3,938,502 | 2/1976 | Bom | 128/2.05 Z X |
| 3,939,696 | 2/1976 | Kossoff | 73/626 |
| 3,954,098 | 5/1976 | Dick et al. | 128/2.05 Z |
| 4,094,306 | 6/1978 | Kossoff | 128/2 V |
| 4,109,642 | 8/1978 | Reid et al. | 128/2 V |

OTHER PUBLICATIONS

Nakashika, M. et al, "Recent Ultrasonic Tomographic System–Sonolayergraph SSL–31A", Toshiba Review, No. 82, 6/73, pp. 13–18.

Primary Examiner—Robert W. Michell
Assistant Examiner—Francis J. Jaworski
Attorney, Agent, or Firm—William A. Drucker

[57] ABSTRACT

An ultra-sonic echography apparatus comprises a probe with multiple elements switched at the rate of transmission pulses and moved along a contour of the test body. Its position is registered by a pantograph cooperating with three sine-cosine potentiometers, the sine potentials of which control the horizontal deflection plates of a cathode-ray tube, while the cosine potentials control the vertical deflection plates and a fourth potentiometer adds potentials displaced by 90° with respect to those delivered by the said three potentiometers, so as to control the beam position of the cathode ray tube for obtaining, on the screen thereof, a beam trace which is homothetic with respect to the ultrasonic beam in the test body.

4 Claims, 4 Drawing Figures

ECHOGRAPHY APPARATUS FOR MEDICAL DIAGNOSIS, USING A MULTIPLE-ELEMENT PROBE

The invention concerns the examination of biological tissues through reflection of ultra-sonic pulses.

In practice this examination is most often effected by applying a method known under the name of type B echography. This method consists of moving the ultrasonic pulse transmitter-receiver probe over the surface of the body following a plane contour and of displaying and/or memorizing, on the target of a cathode-ray tube, the echoes obtained from the plane of this coutour. The probe is moved manually and it is fixed at the end of a pantograph which allows for the registration of its position in space in the course of the movement. The scanning of the cathode-ray tube beam is synchronized by the displacement of the probe in order to obtain a sectional view of the organs examined.

In known apparatus of this type the spatial resolution of the images leaves much to be desired and, as the speed of formation of the image is relatively slow, the woolliness of movement caused either by beats of vascular origin or by the respiratory rhythm contribute to the degradation in the quality of the image.

There is also a recognized method of obtaining a dynamic analysis of cardiac movements in which a probe with multiple elements energized at a high cyclic rate and giving quasi-instantaneous images is used. In this type of apparatus the displacement of the probe is not reproduced on the target or the screen of the display or storage tube, the scanning beam of which is only synchronized with the switching of the probe elements.

The present invention has for its object a medical echography apparatus characterized by the combination of a multiple-element probe, with means for switching at a high cyclic rate the connection of these elements with the transmitting-receiving devices, means for translating the position of the probe in the course of its manual displacement into electrical signals representing this position, and of electronic circuits designed to synchronize the scanning beam of the display or storage tube both with the switching of the probe elements and with the said electrical signals.

Such an apparatus permits a variety of methods of representation of the tissues and thus corresponds to the different needs of medical echography.

According to a preferred embodiment, the said means for translating the position of the probe into electrical signals comprises, in a manner known in itself, a pantograph in which each of the three joints cooperates with a sine-cosine potentiometer the slider of which is driven by the said joint.

More precisely one of the objects of the invention is an apparatus of the kind above referred to, designed to effect in particular a type B echography, in which the multi-element probe is moved along a contour on the surface of the test body, characterized by a commutation of the individual elements of the probe at the transmission frequency of the pulses and by a synchronization of the beam of the display or storage tube such that the beam trace occupies at each moment, on the screen of this tube, a position homothetic with that of the ultrasonic beam in the body, the tube being adjusted to work in an integrating manner so as to give a perceptible image only after several traverses of the beam of the tube over the same position.

It is another purpose of the invention to provide an apparatus of the type above referred to, which is capable of effecting an examination of biological tissues by applying the method known in industrial applications under the name of type C echography.

Type C echography, as it is used in industrial applications, consists of using a focussing probe which is moved over the plane entry surface of an object to be examined and of displaying and/or memorizing, on the target of a cathod-ray tube, the echoes obtained in the interior of the object on a plane parallel to the said surface.

According to this specific embodiment of the invention the multiple-element probe is moved following a contour of the body to be examined contained in a plane perpendicular to the plane of the probe, and the apparatus is characterized by a commutation of the individual elements of the probe and by electronic selection circuits which permit the formation of the image by taking account only of the echoes reflected by obstacles situated in a plane perpendicular to the plane of the said contour and to the plane of the probe.

Another object of the invention is to provide an apparatus of the kind above referred to, which should be capable in addition of effecting the examination of biological tissues in several different sectional planes.

According to this embodiment of the invention, the probe is moved over a contour of the test body perpendicular to its plane, the elements of the probe are divided into several groups, the commutation being effected between the respective groups, in each of which the elements are connected in parallel, the images corresponding to the respective groups being formed either simultaneously or successively.

According to a more specific embodiment, intended for cardiac examination, the images corresponding to the respective groups are formed successively in synchronism with the cardiac rhythm.

The different features, as well as the advantages of the invention, will be clear from the description below.

On the appended drawing:

FIG. 1 shows a multiple-element probe S comprising, for example, 20 ultra-sonic transmitter-receiver piezoelectric elements $S_1$ to $S_{20}$, independent of one another both piezo-electrically and electrically.

Figure 1:
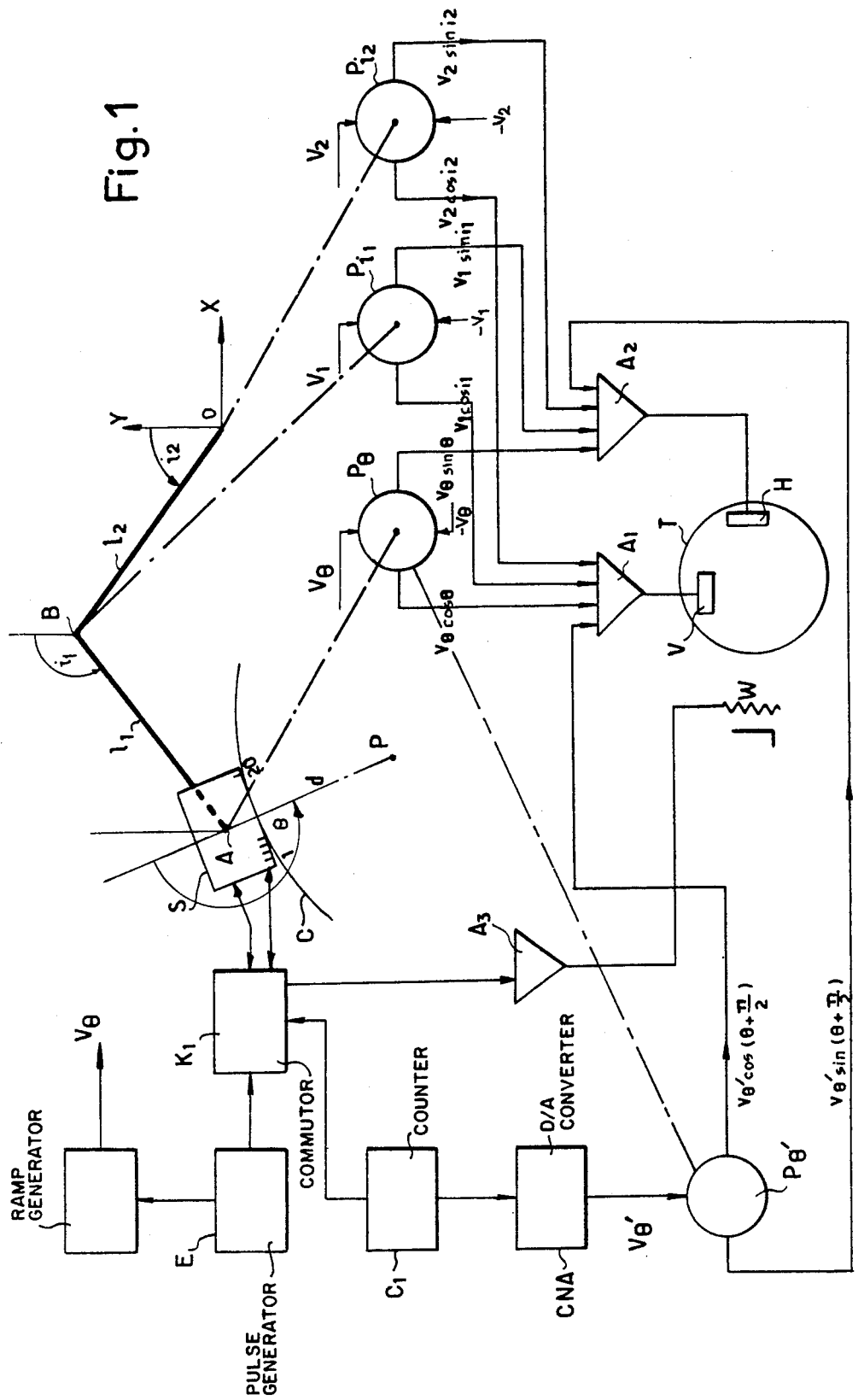
FIG. 1 is a schematic diagram of an apparatus conforming to a preferred embodiment of the invention and illustrates the movement of the probe where it is functioning in the type B scanning mode.

This probe is energized by electrical pulse-transmitting devices symbolized by a rectangle E. The connection between these devices E and the 20 elements of the probe is accomplished by means of an electronic commutator $K_1$. For example, a pulse frequency of 1 kHz is used, and a commutation frequency of 1 kHz, with the result that the beam of ultrasonic waves generated by the probe effects an electronic scanning over the surface of contact with the body examined in about 1/50 second. A relatively slow manual scanning is superposed on this electronic scanning (effected, for example, in several seconds).

On reception the echoes are amplified by an amplifier $A_3$ which drives the control electrode W of a cathode-ray tube of which are represented symbolically the screen T, a vertical deviation plate V and a horizontal deviation plate H.

The probe can be moved manually following a plane contour C of the surface of the patient's body. Its displacement is registered by a pantograph denoted in the drawing by two arms OB and BA of length $l_2$ and $l_1$ respectively. The arm OB is jointed at the fixed point O and makes a variable angle $i_2$ with the vertical. The arm BA is connected at A to the probe by a joint and jointed at B to the arm BO. It makes an angle $i_1$ with the vertical. The direction of radiation AP of the probe makes an angle $\theta$ with the vertical. Sine-cosine potentiometers $Pi_1$ and $Pi_2$, of which the sliders are driven by the joints B and O respectively, generate potentials $V_1 \sin i_1$ and $V_1 \cos i_1$ on the one hand, $V_2 \sin i_2$ and $V_2 \cos i_2$ on the other hand. For this purpose they are fed with steady potentials $(V_1, -V_1)$ and $(V_2, -V_2)$, which are proportional to $l_1$ and $l_2$ respectively.

A sine-cosine potentiometer $P_\theta$, fed with saw-tooth wave potentials $V_\theta$ and $-V_\theta$ synchronized by the transmitted pulses and of which the slope is proportional to the velocity of propagation c of the ultra-sonic waves in the tissue being investigated, has a slider driven by the joint A, in such a manner as to generate two saw-tooth potentials $V_\theta \sin \theta$ and $V_\theta \cos \theta$ respectively, $V_\theta$ being proportional to the product ct representing the distance d between the probe and the point P being examined.

It will be noted that the coordinates of the point A with respect to two axes OX and OY are:

$x_o = l_1 \sin i_1 + l_2 \sin i_2$ and $y_o = l_1 \cos i_1 + l_2 \cos i_2$.

In other words $x_o$ is the sum of the sine potentials from $Pi_1$ and $Pi_2$, while $y_o$ is the sum of the corresponding cosine potentials.

Each of the coordinates x and y of the point P is the sum of the corresponding coordinate $x_o$ or $y_o$ of the point A and of the sine or cosine potential from $P_\theta$.

A counter $C_1$ connected to the commutator K and ensuring control of it, indicates at each moment the number of the piezo-electric element energized. This information is converted to a potential $V_\theta'$ by a digital-to-analogue converter CNA which feeds a sine-cosine potentiometer $P'_\theta$, the slider of which is rigidly connected to that of the potentiometer $P_\theta'$, with a displacement of $(\pi/2)$ between the two spindles. Provided that converter CNA be of proper type or tbe connected to $P_\theta'$, through suitable level shift amplifier means, the potentials delivered by $P_\theta'$ will be:

$$V_\theta', \cos (\theta + \frac{\pi}{2}) \text{ and } V_\theta', \sin (\theta + \frac{\pi}{2}).$$

The cosine potentials from the four potentiometers are applied to a summation amplifier $A_1$, while the sine potentials are applied to a summation amplifier $A_2$.

The output of $A_1$ is connected to H, that of $A_2$ to V, with the result that the cathode-ray tube spot has coordinates:

$$x' = x_o + V_\theta' \sin (\theta + \frac{\pi}{2}) + ct \cos\theta$$

$$y' = y_o + V_\theta' \cos (\theta + \frac{\pi}{2}) + ct \sin\theta.$$

In other words, the spot has a composite deviation resulting from the manual scanning movement $(x_o, y_o)$, the propagation of the ultrasonic waves (ct $\sin \theta$, ct $\cos \theta$) and the rapid displacement of the beam perpendicularly to the direction of propagation $$[V_\theta' \sin (\theta + \frac{\pi}{2}), V_\theta' \cos (\theta + \frac{\pi}{2})].$$

In the course of the composite scanning of the tissue examined by the ultra-sonic beam, each obstacle is detected a large number of times and the resultant images obtained on the screen are, by reason of the divergence of the beams, small hyperbolic arcs which cut one another at a point corresponding to the position of the theoretical point image. The tube is adjusted so as to work in an integrating manner so that it only produces a perceptible image at this point of intersection. In actual fact the image is composed of a spot equal in size to the length of the ultra-sonic pulse transmitted, surrounded by a halo of rapidly diminishing intensity.

Figure 2:
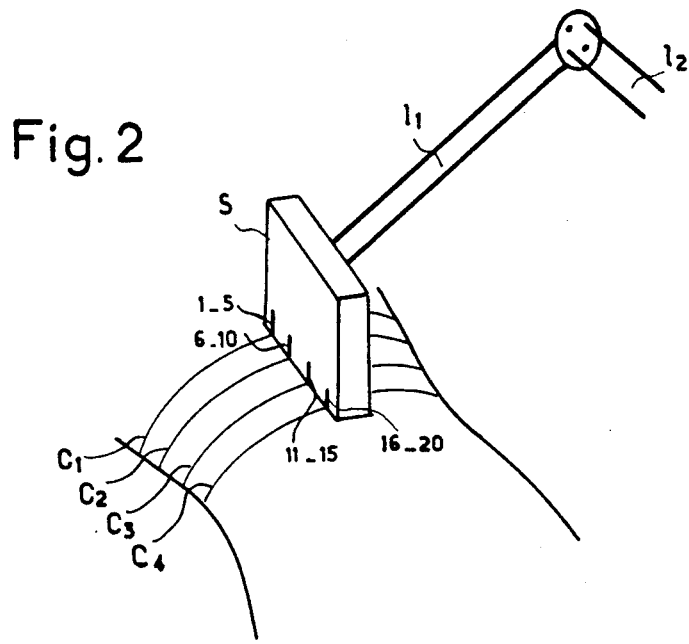
FIG. 2 illustrates the movement of the probe where the mode of operation is intended to obtain successive sectional views of the body examined.

An apparatus of the general type shown in FIG. 1 can, as an alternative, be used as illustrated in FIG. 2, that is by placing the probe in a plane perpendicular to the contour planes $C_1$, $C_2$, $C_3$, $C_4$ of the patient's body, and by moving it manually perpendicularly to its plane. The pantograph $(l_1, l_2)$ moves in this case in a plane parallel to these contours.

The commutator K is then adjusted and regulated so that the elements are commutated in groups of 5, (for example) at the frequency of the transmission pulses, that is: during a first transmission cycle the elements 1–5 are simultaneously energized; (excited in parallel); during the second cycle the elements 6–10 are simultaneously energized etc. The counter $C_1$ and the potentiometer $P'_\theta$, are disconnected in this mode of operation.

As in the preceding embodiment, the potentiometers $P_\theta$, $Pi_1$ and $Pi_2$ deliver sine and cosine potentials of which the respective sums are representative of the coordinates of the point investigated P. This point belongs to the contour $C_1$ during the first cycle, to the contour $C_2$ during the second cycle, etc.

At every commutation there are superposed, by well-known means not shown, direct-current potentials of suitable amplitude on to the potentials applied to the plates H and V of the cathode-ray tube by the amplifiers $A_1$ and $A_2$, so as to deflect the spot in order to form images of the contours $C_1$ to $C_4$ in the different parts of the screen or of the target. The tube T is advantageously of the recording type. The electrical images recorded by known methods can thus be read off and made to appear on a display screen, either one of four images on a larger scale or several superposed images of which the relative intensities have been adjusted so as to distinguish the different sectional planes from one another.

By carrying out the read-off in such a way as to cause the different images to appear successively on the display screen and by synchronizing it with the cardiac rhythm, it is possible to display the phases of the cardiac rhythm in a particularly simple manner.

The apparatus of the general type shown in FIG. 1 can also, as a variant, be used to carry out a type C echography.

For this the probe is arranged and moved as illustrated in FIG. 2, but its elements are commutated individually as has been described in reference to FIG. 1 for the type B echography.

Figure 3:
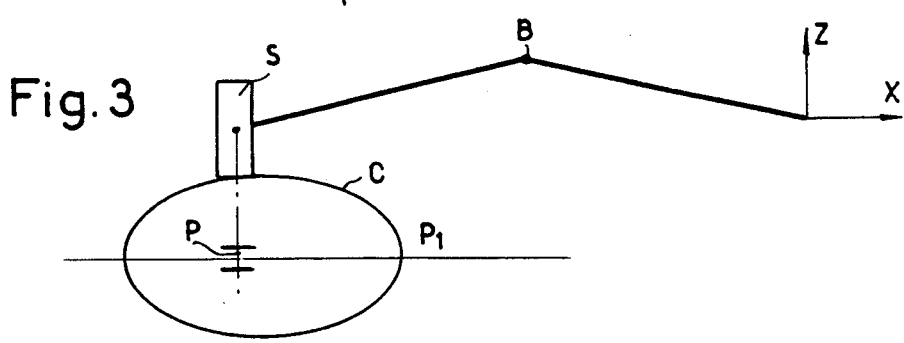
FIG. 3 illustrates the movement of the probe when functioning in the type C scanning mode.
Figure 4:
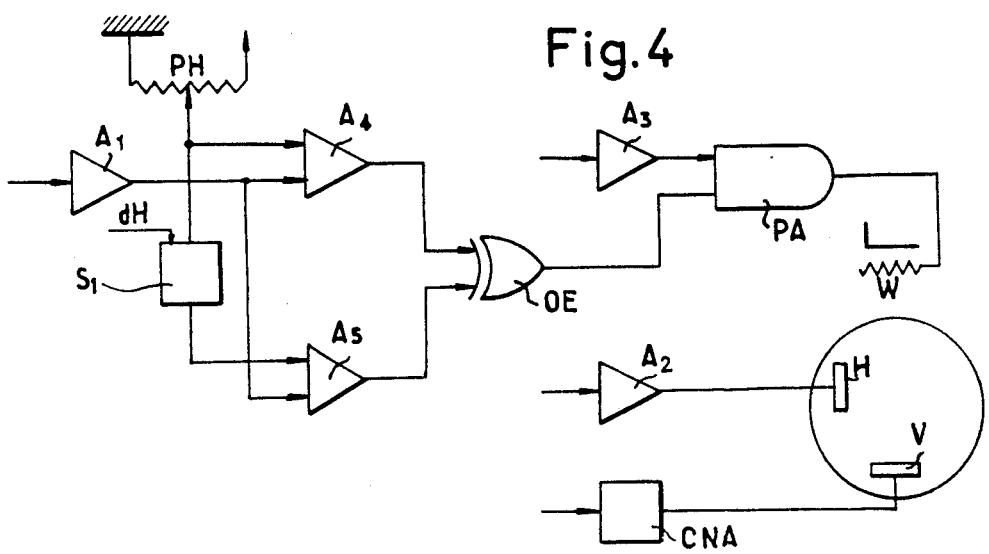
FIG. 4, supplemented by FIG. 1, shows the principle of operation of the apparatus when it functions in the type C scanning mode.

FIG. 3 shows the section of the probe and of the patient's body (contour C) in the plane in which the pantograph arms move. As will be explained below in connection with FIG. 4, the apparatus includes circuits which allow only the echoes reflected by obstacles situated in a plane perpendicular to the plane of the contour C to be taken into account in the formation of an image, the position of this plane (of which the trace $P_1$ has been represented on the plane C) being capable of adjustment by the operator.

The co-ordinates of a point P reached by the ultrasonic pulse at any instant are:

$$x = x_o + ct \sin \theta$$

$$y = y_o + ct \cos \theta$$

$x_o$ and $y_o$ being the values already indicated, and $\theta$ having the same definition as above.

The horizontal deflecting plates H of the cathode-ray tube T (FIG. 4) are supplied with a saw-tooth potential having an amplitude proportional to x. This potential is generated by means of potentiometers $P_\theta$, $P_{i1}$, and $P_{i2}$ and the amplifier $A_2$ shown in FIG. 1, the potentiometer $V_\theta'$ being assumed disconnected. The vertical deviation plates V are fed with a staircase potential of amplitude y proportional to the number of the active element of the probe. This potential is available at the output of the unit CNA of FIG. 1.

The differential amplifier $A_4$ (FIG. 4) receives, on one of its terminals, a saw-tooth potential of amplitude proportional to $y = y_o + ct \cos \theta$. This potential is generated by means of the potentiometers $P_\theta$, $P_{i1}$ and $P_{i2}$ shown in FIG. 1 and of the amplifier $A_1$, the potentiometer $V_\theta'$ being assumed disconnected. On its other terminal, $A_4$ receives a direct-current potential H, regulable by means of a potentiometer $P_H$, and proportional to the distance which separates the horizontal plane $P_1$ from a horizontal reference plane.

A differential amplifier $A_5$ also receives the output potential of the amplifier $A_1$. On its other terminal it receives a potential H+dH which is the summation, carried out by unit $S_1$, of the potential H and a supplementary direct-current potential dH of amplitude small in comparison with H, which defines a thickness of the zone to be investigated around the section plane P1.

The outputs of the amplifiers $A_4$ and $A_5$ are connected to the two inputs of an exclusive OR circuit OE, the output of which is connected to one input of an analogue gate PA. The other input of A is connected to the receiving amplifier $A_3$ of FIG. 1.

The circuit OE delivers a signal when the potentials delivered by $A_4$ and $A_5$ have different polarities, i.e. when the ordinate of the point P lies between the levels H and H+dH. When this is the case the gate PA transmits the echo signals to the electrode W of the cathode-ray tube. In the way a zone of investigation of adjustable thickness and position has been defined.

In the horizontal plane $P_1$ investigated in this way, the combination of the manual displacement of the probe parallel to the axis OX and of the electronic scanning by the commutation of the elements following an axis OY perpendicular to OX gives a representation in section conforming to the traditional representation of type C. Because of the fact that the structures analysed are usually at a relatively constant distance from the probe, one will generally choose the geometrical characteristics of the latter in such a way that it will generate a beam focussing at this distance.

It has been possible to obtain resolutions of the order of a millimeter by this procedure.

The invention is not limited to the modes of operation described above. In particular, instead of registering the movements of the probe by means of a pantograph one could use a registering device in the form of a tracing table (which would, however, be more complicated).

What is claimed is:

1. Apparatus for medical B type echography, comprising: transmitter means for generating and transmitting recurrent high frequency electric pulse trains; a linear array of individual transducer means connected to said transmitter means for converting the said electric pulse trains into a beam of acoustic pulses which are reflected from test points within the body under examination so as to produce acoustic echoes, said transducer means also converting the acoustic echoes into electric echoes; receiver means having an input connected to said transducer means and an output; a cathode-ray tube having a control electrode connected to the output of the receiver means, and first and second deflection electrodes for respectively controlling the horizontal and vertical deflection of a writing beam, the said cathode-ray tube operating in an integrating manner so as to form a perceptible image of any test point only after several traverses of the acoustic pulse beam at the said point; the respective transducer means having a common support member on which they are fixedly mounted; switching means, controlled from the said transmitter means, for successively connecting one by one the successive individual transducer means to the transmitter means at the repetition rate of said recurrent electric pulses, whereby the said beam of acoustic pulses is translated in a direction perpendicular to the said beam from one position of translation to another; pantographic means for effecting manual displacement of the support member with respect to the said body, said pantographic means having first and second arms, a first joint connecting the first and second arms together, the second arm having a fixed end opposite to the first joint, a second joint connecting the end of the first arm opposite to the first joint to the said support member; a first sine-cosine potentiometer having a first sine output, a first cosine output and a first slider which is connected to the first joint; a second sine-cosine potentiometer having a second sine output, a second cosine output and a second slider, a third joint connecting the said fixed end of the second arm to the second slider; means for supplying the first potentiometer with a direct-current voltage proportional to the length of the first arm; means for supplying the second potentiometer with a direct-current voltage proportional to the length of the second arm; a third sine-cosine potentiometer having a third sine output, a third cosine output and a third slider; means for supplying the third potentiometer with a saw-tooth voltage having a slope proportional to the velocity of propagation of the acoustic waves within the said body, the said supplying means being connected to the said transmitting means whereby the frequency of said saw-tooth wave is the pulse repetition frequency, the said third slider being connected to the second joint; a first summing amplifier having an output which is connected to the said first deflection electrode and first, second and third inputs respectively connected to the first, second and third sine outputs; a second summing amplifier having an output which is connected to the said second deflection electrode and first, second and third inputs respectively connected to the first, second and third cosine outputs; counter means, connected to said transmitter means and to said switching means, for providing a digital count indicative of the individual transducer means which is connected to the transmitting means; means for converting the said count into an analog direct-current potential indicative of the said position of translation of the beam; a fourth sine-cosine potentiometer having fourth sine and cosine outputs and a fourth slider, means for rigidly connecting the fourth slider to the third slider with a constant relative angular offset of 90°; the first and second summing amplifiers each having a fourth input, the said fourth input being respectively connected to the fourth sine output and the fourth cosine output of the fourth potentiometer.

2. Apparatus for inspecting, in a plurality of sectional parallel planes, a body under examination, comprising: transmitter means for generating and transmitting recurrent high frequency electric pulse trains; a linear array comprising a plurality of groups of individual transducer means connected to said transmitter means for converting the said electric pulse trains into a beam of acoustic pulses which are reflected from test points within the body under examination so as to produce acoustic echoes, said transducer means also converting the acoustic echoes into electric echoes; receiver means having an input connected to said transducer means and an output; a cathode-ray tube having a screen, a control electrode connected to the output of the receiver means, and first and second deflection electrodes for respectively controlling the horizontal and vertical deflection of a writing beam, the respective transducer means having a common plane support member on which they are fixedly mounted; switching means, controlled from the said transmitter means, for successively establishing a plurality of configurations of the connections between the respective transducer means and the transmitter means at the repetition rates of said recurrent electric pulses, all the individual transducer means of one of said groups being connected in parallel to the transmitter means for each of said configurations and the switching from one configuration to another corresponding to a shifting to the next group and to a translation of the said beam of acoustic pulses in a direction perpendicular to the said sectional planes from one position of translation in which the said beam is located in one sectional plane to another in which the said beam is located in another sectional plane; pantographic means for effecting manual displacement of the support member with respect to the said body, with the support member perpendicular to the said sectional planes, said pantographic means having first and second arms, a first joint connecting the first and second arms together, the second arm having a fixed end opposite to the first joint, a second joint connecting the end of the first arm opposite to the first joint to the said support member; a first sine-cosine potentiometer having a first sine output, a first cosine output and a first slider which is connected to the first joint; a second sine-cosine potentiometer having a second sine output, a second cosine output and a second slider, a third joint connecting the said fixed end of the second arm to the second slider; means for supplying the first potentiometer with a direct-current voltage proportional to the length of the first arm; means for supplying the second potentiometer with a direct-current voltage proportional to the length of the second arm; a third sine-cosine potentiometer having a third sine output, a third cosine output and a third slider; means for supplying the third potentiometers with a saw-tooth voltage having a slope proportional to the velocity of propagation of the acoustic waves within the said body, the said supplying means being connected to the said transmitting means whereby the frequency of said saw-tooth wave is the pulse repetition frequency, the said third slider being connected to the second joint; a first summing amplifier having an output which is connected to the said first deflection electrode and first, second and third inputs respectively connected to the first, second and third sine outputs; a second summing amplifier having an output which is connected to the said second deflection electrode and first, second and third inputs respectively connected to the first, second and third cosine outputs; and means for shifting the writing beam each time a group of individual transducers is shifted, whereby several images from the body under examination are displayed on different parts of the said screen.

3. Apparatus for medical C type echography, comprising: transmitter means for generating and transmitting recurrent high frequency electric pulse trains; a linear array of individual transducer means connected to said transmitter means for converting the said electric pulse trains into a beam of acoustic pulses which are reflected from test points within the body under examination so as to produce acoustic echoes, said transducer means also converting the acoustic echoes into electric echoes; receiver means having an input connected to said transducer means and an output; a cathode-ray tube having a control electrode connected to the output of the receiver means, and first and second deflection electrodes for respectively controlling the horizontal and vertical deflection of a writing beam; the respective transducer means having a common plane support member on which they are fixedly mounted; switching means, controlled from the said transmitter means, for successively connecting one by one the successive individual transducer means to the transmitter means at the repetition rate of said recurrent electric pulses, whereby the said beam of acoustic pulses is translated in a direction perpendicular to the said beam from one position of translation to another; pantographic means for effecting manual displacement of the support member with respect to the said body, said pantographic means having first and second arms, located in a plane, a first joint connecting the first and second arms together, the second arm having a fixed end opposite to the first joint, a second joint connecting the end of the first arm opposite to the first joint to the said support member, the said support member being mounted perpendicular to the said plane; a first sine-cosine potentiometer having a first sine output, a first cosine output and a first slider which is connected to the first joint; a second sine-cosine potentiometer having a second sine output, a second cosine output and a second slider, a third joint connecting the said fixed end of the second arm to the second slider; means for supplying the first potentiometer with a direct-current voltage proportional to the length of the first arm; means for supplying the second potentiometer with a direct-current voltage proportional to the length of the second arm; a third sine-cosine potentiometer having a third sine output, a third cosine output and a third slider; means for supplying the third potentiometer with a saw-tooth voltage having a slope proportional to the velocity of propagation of the acoustic waves within the said body, the said supplying means being connected to the said transmitting means whereby the frequency of said saw-tooth wave is the pulse repetition frequency, the said third slider being connected to the second joint; a first summing amplifier having an output which is connected to the said first deflection electrode and first, second and third inputs respectively connected to the first, second and third sine outputs; a second summing amplifier having an output which is connected to the said second deflection electrode and first, second and third inputs respectively connected to the first, second and third cosine outputs; counter means, connected to said transmitter means and to said switching means, for providing a digital count indicative of the individual transducer means which is connected to the transmitting means; means for converting the said count into an analog direct-current potential indicative of the said position of translation of the beam, said means for converting the count into an analog direct-current potential being connected to the said second deflection electrode; the said first summing amplifier being connected to the first deflection electrode; and electronic selection circuits connecting the second summing amplifier to the control electrode and selecting only the echoes formed within the body under examination in a plane at right angles with the said plane.

4. An apparatus according to claim 3, wherein the said electronic selection circuits comprise a first differential amplifier having a first input connected to the output of the second summing amplifier, a second input and an output; means, connected to the second input of the first differential amplifier for generating a first direct-current reference voltage; a second differential amplifier having a first input connected to the output of the second summing amplifier, a second input and an output; means, connected to the second input of the second differential ampifier, for generating a second direct-current reference voltage having an amplitude which differs from the amplitude of the first direct-current reference voltage from a quantity which is small with respect to the said amplitude; an EXCLUSIVE OR gate having an output and first and second inputs which are respectively connected to the outputs of the first and second differential amplifiers and an analog gate having a first input connected to the output of the EXCLUSIVE OR gate, a second input connected to the said receiver means and an output which is connected to the control electrode.

* * * * *